United States Patent [19]

Powell

[11] Patent Number: 5,256,298
[45] Date of Patent: Oct. 26, 1993

[54] CONTINUOUS-BELT SEPARATOR/REACTOR AND METHOD

[76] Inventor: Paul E. Powell, 4159 Steck Ave. #125, Austin, Tex. 78759

[21] Appl. No.: 872,638

[22] Filed: Apr. 22, 1992

[51] Int. Cl.$^5$ .................. B01D 15/00; B01D 15/02
[52] U.S. Cl. .................. 210/660; 210/679; 210/763; 210/263; 210/400; 210/401; 210/615
[58] Field of Search ............. 210/656, 660, 676, 401, 210/198.2, 924, 400, 679, 763, 615; 134/70, 73, 75, 127, 201, 95; 261/80

[56] References Cited

U.S. PATENT DOCUMENTS

| | | | |
|---|---|---|---|
| 2,678,132 | 5/1954 | Beard, Jr. | 210/42.5 |
| 3,613,564 | 10/1971 | Wheeling | 210/401 |
| 3,617,552 | 6/1971 | Will et al. | 210/23 |
| 3,640,394 | 2/1972 | Brill et al. | 210/924 |
| 3,679,058 | 7/1972 | Smith | 210/242.4 |
| 3,907,685 | 9/1975 | Aramaki et al. | 210/924 |
| 3,910,842 | 10/1975 | Karlson | 210/252 |
| 3,986,959 | 10/1976 | Bagot et al. | 210/924 |
| 4,027,400 | 6/1977 | Erickson | 210/774 |
| 4,548,802 | 10/1985 | Dickey | 423/659 |
| 4,548,803 | 10/1985 | Dickey | 423/659 |
| 4,599,225 | 7/1986 | Dickey | 210/656 |
| 4,726,903 | 2/1988 | Dickey | 210/656 |
| 4,740,310 | 4/1988 | Dickey | 210/649 |
| 4,761,236 | 8/1988 | Dickey | 210/656 |
| 4,940,134 | 7/1990 | Aoki et al. | 210/774 |
| 5,015,378 | 5/1991 | Lewan et al. | 210/386 |

FOREIGN PATENT DOCUMENTS 2223 2/1951 Japan .

OTHER PUBLICATIONS

Erdos, E. & G. Szekely, 1982, J. Chromat. 241:103–112.
Karlson, E. L. & S. P. Edkins, 1975, AICHE Symp. Ser. 151:286–291.
McCormack, R. H. & J. F. Howard, 1953, Chem. Engin. Prog. Aug. 1953:404.
Muendel, C. H. & W. A. Selke, 1955, Ind. Engin. Chem. 47:374–379.
Srikameswaran, K. & H. D. Gesser, 1978, J. Environ. Sci. Health A13:415–427.
Vernon, F. & T. Shah, 1983, Reactive Polym. 1:301–308.
Bowen, H. J. M., J. Chem. Soc. (A) 1970:1082–1085.
Braun, T., 1989, Fresenius Z. Anal. Chem. 333:785–792.
Braun, T. & A. B. Farag, 1973, Anal. Chim. Acta 65:139–145.
Charm, S. E. & B. L. Wong, 1978, J. Macromol. Sci.--Chem. A10:53–71.

Primary Examiner—Stanley S. Silverman
Assistant Examiner—Cynthia L. Nessler

[57] ABSTRACT

An apparatus and method for substantially eliminating diffusion and resin capacity as rate-limiting factors in mass transfer between phases in separation, chemical reaction, and biological culture processes by establishing turbulent flow of fluids within a continuous, moving belt of resilient, open-cell foam polymer. The belt is made to move alternately between bulk liquid and gas phases where mass transfer takes place by direct transport to the polymer surface as a consequence of compression and release of the belt.

16 Claims, 3 Drawing Sheets

CONTINUOUS-BELT SEPARATOR/REACTOR AND METHOD

BACKGROUND OF THE INVENTION

1. Field of the Invention

This invention relates to the fields of separation technology and chemical- and bio-reactor technology and more particularly to continuous methods and apparatus employing endless belts of resilient, open-cell foam polymers such that diffusion and resin capacity are not limiting factors in mass transfer between phases.

2. Separations by Sorption Resins

The separation and purification of chemicals by selective sorption on solid material has been known from ancient times when wine and olive oil were filtered through charcoal to remove impurities. Materials science has created a great variety of porous, organic and inorganic materials with large internal surface areas and with functional groups designed for selective sorption of chemicals according to their specific physical and chemical properties. Industrially useful solute sorption processes include: adsorption to surfaces by non-specific London/van der Waals forces, as with charcoal; electrostatic attraction of charged ions to oppositely charged functional groups, as on ion-exchange resins; interaction of hydrophobic regions of molecules with hydrocarbon pendant groups on resins; attraction of metal-dependent enzyme proteins to atoms of those metals held to resins by chelation or coordination; hydrogen bonding of proteins and nucleic acids through the interaction with polar oxygen- and nitrogen-containing groups on resins; and biospecific affinity of proteins to substrates, cofactors, antibodies, antigens, receptors, toxins or biomimetic dyes bound to resins.

DIFFUSION LIMITATION IN PRIOR ART

Porous particulate materials are used in most industrial chemical separations based on sorption phenomena. The separation of a product ion or molecule from solvent and from other solutes during resin loading and elution requires the following steps:

1. diffusion of the product from the bulk solution through the laminar film of solution surrounding the particle to the particle surface;
2. diffusion of the product through tortuous pores to the binding site on the interior of the particle;
3. sorption reaction of the product at the binding site;
4. diffusion of the eluent from the bulk solution through the laminar film to the particle surface;
5. diffusion of the eluent through the pores to the binding site;
6. desorption reaction of the product at the binding site;
7. diffusion of the product through the pores to the particle surface;
8. diffusion of the product through the surface film to the bulk solution.

In the vast majority of industrial sorption processes, pore diffusion is the rate-limiting step. However, in cases of dilute solutions of small ions or molecules, film diffusion can sometimes be limiting. Sorption and desorption reaction rates are generally very fast; they are, in fact, usually not considered in estimations of overall process rates.

USE OF RESILIENT OPEN-CELL FOAM POLYMERS

Analytical chemists have found a sorption material and method which eliminates diffusion as the limiting factor in the concentration and purification of many organic and inorganic compounds from solution. Since 1970 (Bowen, 1970) resilient, open-cell polyurethane foams have been used for the separation of metals, including gold, uranium, gallium and the platinum group elements among others, and for the concentration of organic compounds including polychlorinated aromatic pesticides as well as enzyme and antibody proteins. Redox reactions have also been carried out on foam supports. These analytical applications have been performed with unmodified polyurethane foam, derivatized foam and foam loaded with solvents, ligands, catalysts, and reagents.

PULSED COLUMN

The pulsed column method of using polyurethane foams was developed by Tibor Braun in 1973 (Braun and Farag, 1973). In this method, the foam is repeatedly compressed and released in the presence of a solution. The foam quickly approaches sorption equilibrium with the solute, frequently in as few as two to five pulses. The effect of residence time of the aqueous phase in the foam of the pulsed column during any particular pulsation was found to be insignificant (Braun and Palagyi, 1979). This time invariance is proof that the process is not diffusion limited. An automated column pulsing apparatus was disclosed in 1978 (Srikameswaran and Gesser, 1978) and "calendar-mangler" equipment for squeeze-contacting polyurethane foam rings with aqueous solutions was described by Tibor Braun in 1989 (Braun, 1989). Both of the above are batch processes.

FOAM RESINS NOT COMMERCIAL SUCCESS

In spite of four extensive reviews citing literally hundreds of examples of chemical separations using resilient, open-cell polymer foams, industrial applications of this material for chemical separations have been virtually nonexistent (Moody and Thomas, 1982; Braun, 1983; Braun, Navratil, and Farag, 1985; and Braun, 1989). The lack of commercial exploitation of resilient, open-cell foam polymers in industrial separation technology can be explained by considering the characteristics of the ideal sorption resin according to text and reference books in the field. The general understanding is that the ideal industrial resin should have the following characteristics:

1. The resin should be rigid to avoid attrition due to breakage;
2. The resin should have a large capacity to avoid the need for frequent regeneration; and
3. The resin should have a large surface area to provide for rapid exchange reactions ($> 100$ m$^2$/g).

Resilient open-cell polymer foams, on the other hand:

1. are flexible by definition;
2. sometimes have limited capacity at equilibrium, as shown by the fact that solute distribution ratios between the resin and the solution are more favorable in dilute solutions (Bowen, 1970); and
3. have a surface area of approximately 0.008 m$^2$/g, four orders of magnitude less than the lowest commercial resins (Gesser and Horsfall, 1977). Another factor that makes the use of polymer-foam sorbents unattractive to the well-trained engineer is the understanding in common chromatographic practice that turbulence is to be avoided. Turbulent flow is turned to advantage by the use of open-cell foams, although this factor appears not to be recognized even by analytical chemists who use the material.

CONTINUOUS BELT

Chemical engineers have long sought to overcome the inefficiencies of fixed-bed, batch, sorption processes. The long cycle times resulting from diffusion limitations, and the requirements for excess sorbents and eluents resulting from diffusion and capacity limitations of the resins, can in some cases be partially off-set by making a process continuous. One approach which attracted much interest in the 1950's and 1960's involves the use of continuous belts packed with sorbent particles, coated with sorbent material, or woven from sorbent fibers (Mihara and Terasaki, 1951; McCormack and Howard, 1953; Beard, 1954; Muendel and Selke, 1955; Karlson and Edkins, 1975; Charm and Wong, 1976; Hughes and Charm, 1979; Erdos and Szekely, 1982; Vernon and Shah, 1983; Dickey, 1985). Generally, in these processes the belt is run through a feed solution and washed, then passed between a set of rollers to remove excess liquid. The belt is subsequently run through a desorption tank, then washed again. Following passage between another set of rollers to remove excess liquid, the belt re-enters the feed solution to complete the cycle. This is a truly continuous system and therefore should, theoretically, have the benefits of consistent product quality, ease of control, and reduced time, space, energy, labor and resin requirements. The equipment is relatively simple and inexpensive compared to the sophisticated three- or four-way valves and electronic control systems required by other continuous and semi-continuous processes.

BELT NOT COMMERCIAL SUCCESS

Several problems have, however, been encountered with attempts to implement continuous-belt sorption systems. The most advanced of such systems (Hughes and Charm 1979) failed because of slow diffusion of solute into and out of the belt and its particulate resin, and because of resin compaction and fluid by-pass. According to P. C. Wankat, "The major problem is that mass transfer rates tend to be very low. It is difficult to force high velocity contact of the fluid and the solid, and fluid by-passing is a problem . . . . The belt adds an additional mass transfer resistance which can be significant. Thus, long residence times and a significant amount of sorbent may be required" (Wankat, 1986). In addition to the problems listed above which result from diffusion limitations, there is often mixing of solutions retained in the interstices and within resin pores between steps. Wankat (1986) expressed his pessimism over the future of moving-belt systems and noted the declining interest, but further stated, "Of course, a clever inventor might develop a simple moving equipment system which would capture a large market."

POLYURETHANE BELT

Another use of continuous-belts has been proposed (e.g. Lewan et al, 1991): that is, the physical removal of oil from water surfaces by passive loading of the belt with oil as it passes through the oil-water interface followed by physical removal of the oil by running the belt through squeeze rollers. One such system employs a polyurethane belt (Will and Grutsch, 1971). Tibor Braun (Braun et al., 1985), who invented the pulsed column method, discussed the 1971 polyurethane-belt apparatus of the Will and Grutsch patent, and Moody and Thomas (1982) prominently illustrated the apparatus in their book on separation applications of foamed polymers. Both works also included illustrations and discussions of the pulsed column which is loaded by compressing the foam and releasing it in the presence of the feed solution. In a later work, Braun (1989) illustrated the latest polyurethane foam sorption techniques including his batch separation process in which a foam ring is contacted with solution by compression between two cylinders.

NO COMBINATION OF PULSED COLUMN AND BELT

To date, no one has disclosed how the compression/release loading of resilient open-cell foam polymers might be performed with an endless-belt apparatus to make it a continuous process. Indeed, no one has even suggested that it would be beneficial to do so. From the foregoing evidence it is clear that the present invention is unobvious even to those most skilled in the art.

GAS/LIQUID MASS TRANSFER

The transfer of molecules from a gas phase to a liquid phase is a common process in industrial product recovery and gas purification—for example, the removal of carbon dioxide and hydrogen sulfide from synthesis gas streams by absorption in diglycolamine. The opposite physical process, transfer of molecules from a liquid phase to a gas phase, includes evaporation, distillation purification and removal of a solute from a liquid by stripping—for example, removal of trichloroethane from ground water. In most industrial applications a solid, column-packing material supports a large liquid film surface over which gas passes. In all of the above-mentioned liquid/gas mass transfer processes, the amount of surface area of the liquid is traditionally considered to be the limiting rate factor for mass transfer reactions at a given temperature and pressure. The mass transfer rate between phases is, in fact, proportional to the interfacial area between the phases. Therefore, any method that maximizes the proportion of fresh interfacial area per unit time would improve process efficiency.

WATER DEMINERALIZATION

The production of large volumes of ultra-pure water for the electronic and biotechnology industries is frequently accomplished by mixed beds of cation- and anion-exchange resin particles. Since both resins are in the same bed, the only product of the deionization reaction is water. The reaction therefore goes to completion and there is no back reaction. The process is, however, discontinuous because the two types of resin must be separated for regeneration and then remixed. In addition to the mechanical complexity of the operation, there is some loss of regenerant chemicals and resin efficiency if resin separation is not complete. Ideally the process should be made a continuous process with the continuous separation and regeneration of the two resins.

BIOREACTORS

In bioreactor technology, the immobilization of shear-sensitive plant and animal cells, as well as the immobilization of bacteria, yeasts and filamentous fungi, has increased production of biological chemicals (e.g. antibodies, hormones, enzymes and antibiotics) and has simplified downstream processing of the products. The growth of cells in macroporous particles and entrapment within gel microcarriers have been the most commonly used methods of immobilization. The diffusion of nutrients and especially oxygen to the cells has, however, proven to be the limiting factor in the productivity of these systems. The recent popularity of open-cell polyurethane foams as support structures in immobilized cell systems is due, in part, to the better oxygen supply available to cells growing on the membrane surfaces within the foam. However, these stationary systems still encounter the universal problem of gradients of nutrients, oxygen, pH, toxins, products, and waste products that develop as the aqueous supply solution traverses the reactor. The gradients result in uneven cell growth and productivity. A process which provides for a continuous, uniform supply of nutrients and removal of wastes and products, as well as providing for unrestricted oxygen and heat transfer, is needed to optimize the industrial production of biological chemicals by living cells.

SUMMARY OF THE INVENTION

Brief Description

The present invention provides an apparatus and a method for carrying out continuous separations and continuous chemical and biological reactions using moving belts of resilient open-cell foam polymer in such manner that diffusion and resin capacity are, generally, not rate limiting in mass transfer between phases. The belt is made to move alternately between bulk liquid and gas phases where mass transfer takes place by direct transport of bulk fluids to the polymer surface as a consequence of continuous compression and release of the belt.

In its preferred embodiment, the invention is effected by compressing and releasing a moving foam belt while it is submerged in suitable liquids and by compressing and releasing the belt in the absence of liquid as it moves through each cycle. Sets of pressure rollers or static members may be used to accomplish the compression. Many useful variations of the invention, including multiple compression and release steps in each of several fluids, exist within the scope of the present invention and will become apparent from the disclosure and examples set forth below.

Theory of Operation

I believe that micro-eddies resulting from the turbulent flow of fluids through the quasi-spherical cells of the foam during compression and following release of compression are responsible for the direct mass transfer of ions and molecules from the bulk fluid phase to the solid membrane of the foam, thus eliminating diffusion as a rate-limiting step. Empirical observations have been reported that tend to support this theory. However, the validity of the invention is not dependent on the verity of any particular theory.

The effective surface area of the foam resin is greatly increased under turbulent flow conditions by the continuous generation of fresh solid/fluid interface due to the rapid presentation of fresh bulk phase fluid to the solid membrane surface. The rate of mass transfer per unit surface area of resin is thus greatly increased.

The fact that the moving belt continuously presents fresh resin surface to each fluid phase in a process means that the system does not reach equilibrium; thus capacity need not be a limiting factor in mass transfer. The constant regeneration of fresh resin by belt movement and the presentation of fresh fluid phase at the resin membrane by turbulent flow more than compensate for the somewhat limited surface area per unit mass of resin.

Belt Materials

Methods exist to fabricate open-cell foams from virtually any synthetic polymer material. Foamed products are already produced from polyvinylchloride (PVC), low-density polyethylene (LDPE), urea resins, acrylate-butadiene-styrene (ABS), and polyurethane (PU). Resilience or flexibility can generally be increased by reducing the degree of crosslinking and, in the case of block polymers, by increasing the proportion of soft block segments and the number of certain chain extenders within hard block segments.

The term "open-cell" as used herein includes resilient polymer foams of any degree of reticulation appropriate for a particular application. According to the present invention, the belt may be reinforced by material of higher tensile strength, or the external surfaces of the belt may be protected by material of higher abrasion resistance.

Polymer material for belts can be modified during synthesis by incorporating functional pendant groups into the polymer chain. After fabrication, ligands, catalytic groups and the like may be incorporated by grafting them onto the polymer. Ligands, solvents, reagents, catalysts and the like can be dissolved in the polymer. Examples include chemically reactive groups such as sulfhydryl groups and also strong and weak ion exchange groups, hydrophobic groups, chelators, coordination compounds, organic solvents, and acid or metal catalysts. Among useful bioaffinity groups that can be incorporated into the belts are enzymes, substrates, cofactors, antigens, antibodies, hormones, receptors, carbohydrates, carbohydrate specific proteins, toxins and biomimetic dyes.

Polyurethane Foam Natural PUF

Resilient open-cell polyurethane foam (PUF) has been selected for the embodiments of the present invention described herein because it is inexpensive and readily available in a variety of compositions. It should be noted, however, that the invention embraces the use of continuous belts made from any resilient open-cell foam polymer.

Bowen (1970) and Braun and Farag (1972) examined the chemical resistance of commercial PUFs and found that they were essentially "unaltered by water, hydrochloric acid up to 6M, sulfuric acid up to 2M, glacial acetic acid, 2M ammonia, and 2M sodium hydroxide solutions, as well as by solvents such as light petroleum, benzene, carbon tetrachloride, chloroform, diethyl ether, di-isopropyl ether, acetone, isobutyl methyl ketone, ethyl acetate, isopentyl acetate, and alcohols." Polyurethane also has very good resistance to seawater and moderately good resistance to deterioration by gamma radiation. The polyether forms are highly resistant to microbial degradation.

Polyurethane is recognized as having the greatest tensile strength, tear resistance, and abrasion resistance among the commonly available elastomers; these are precisely the physical characteristics required of durable belts. It is recognized than for some applications the belts may need to be reinforced with material of higher tensile strength or have their surfaces protected by a more abrasion-resistant material.

The chemical characteristics of PUF also are suited to separations performed according to the present invention. Untreated PUF can act as a sorption resin through many different mechanisms depending upon the chemical environment. For example, polyether PUF behaves as a solid solvent with absorption characteristics similar to diethyl ether in some cases—e.g. the extraction of uranyl nitrate from nitrate solutions and the extraction of polychlorinated aromatic compounds from water. Plasma proteins are adsorbed by hydrophobic interaction with the non-polar soft segments of some PUFs. Hydrogen bonding occurs with the oxygen and nitrogen atoms of the urethane, allophanate and biuret groups in the polar, hard segments of PUF. In strong acid solutions, PUF behaves as an anion exchange resin of variable strength because of the tendency of both the ether-oxygen atoms and the various nitrogen-containing groups to accept protons and thus acquire a positive charge with a range of strengths. All of the above sorption reactions of unmodified PU foams are reversible by swings in chemical conditions.

Modified PUF

Polyurethane foams can be modified in several ways to accomplish a variety of sorption reactions. Commercial ion exchange resins have been powdered and added to PUF synthesis mixtures. Activated carbon and lignins have also been physically incorporated. PUF impregnated with reagents such as tri-n-butyl phosphate, dithiazone, tri-n-octylamine and the like have found use in hydrometallurgy. Specific functional groups have been either grafted on to PUF or incorporated into the polymer as chain extenders. Sulfhydryl groups, antibodies and enzymes are examples of useful groups grafted to PUF. Ionomers that have been incorporated into PUF during synthesis include tertiary and quaternary amines as well as thiosulfate, sulfonate, carboxylate and phosphoric acid groups among others. Recently, such metal-coordinating groups as macrocyclic or crown ethers have been included in PUF synthesis mixtures, suggesting their use in metal-catalyzed reactions. Hydrophobic pendant groups like the C-eight to C-16 hydrocarbons can be grafted to PU for reverse-phase or hydrophobic-interaction separations. From the above cited examples, it is clear that the chemical modifications to resilient, open-cell polyurethane foams can be made to accommodate a wide range of separation and reaction processes according to the present invention.

Applications of Invention

Those skilled in the art will recognize in the present invention the possibility of many and diverse applications in various fields including the chemical process industry, water treatment, environmental remediation, hydrometallurgy, and biotechnology among others. A few of these applications, their advantages over prior art, and some unexpected benefits are described below.

Embodiment for Separation of Solutes

Figure 1A:
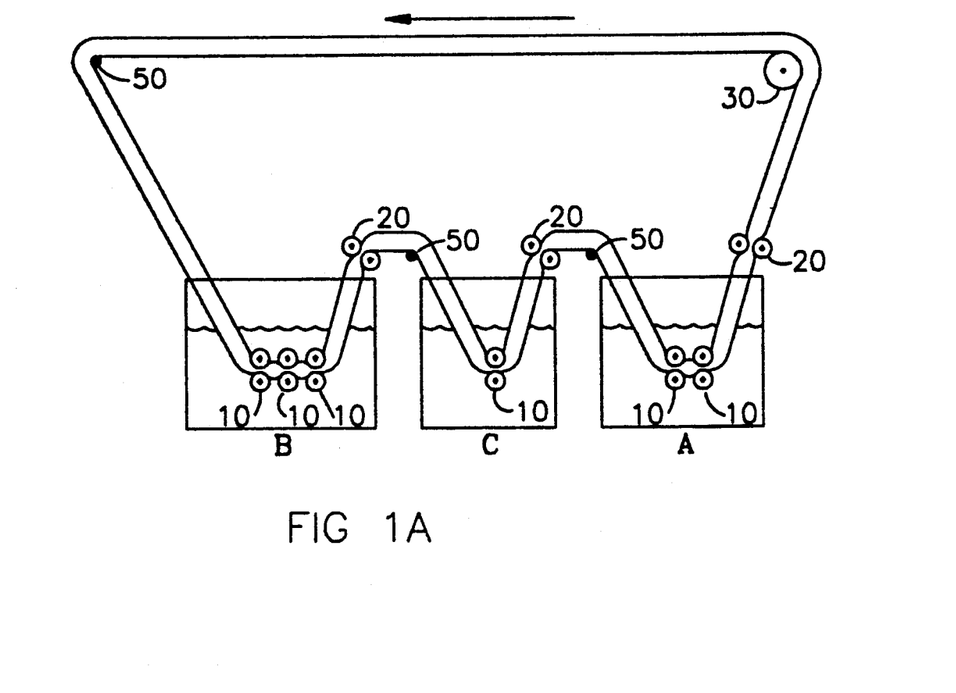
FIG. 1a shows a longitudinal section of a preferred embodiment of the present invention for the separation of similar chemicals by a sorption process.

A preferred embodiment of the present invention is for use in the separation and purification of similar chemical species from solution—e.g. proteins or precious metals—as illustrated in FIG. 1a. Unmodified PUF belts or PUF belts loaded with a chelator or water-immiscible reagent, or modified with hydrophobic, bioaffinity or ionic pendent groups, can be used.

The belt enters a feed tank. With the more reticulate foams, the pores are passively filled upon entering the liquid, thus avoiding foaming problems which frequently result from the violent mixing of gases and liquids especially when surface active compounds such as proteins or fatty acids are present.

Feed solution can be introduced into the tank along the entire length of the tank, thus providing uniform uptake conditions and maximum resin loading. On the other hand, if the feed solution is introduced at one end of the tank, then solution flow rate and belt speed can be adjusted so that a completely exhausted solution exits at the opposite end of the tank. In this mode, many of the advantages of countercurrent flow obtain, with the chemical having the greatest affinity for the resin being sorbed at the proximal side of the belt and the chemical having the least affinity being sorbed, without competition, at the distal side of the belt. This cross-flow mode of operation is especially useful in removing mixed toxic wastes from water when there is a zero concentration tolerance for the effluent. True countercurrent conditions can be established by the use of multiple feed tanks connected in series. Countercurrent conditions can also be established by use of a plurality of sets of pressure rollers in a single narrow deep tank with a baffle separating the entering and leaving portions of the belt. The flexibility of alternate loading modes is not offered by any prior art.

When the moving belt is compressed as it passes through the nip of the pressure rollers, the liquid resident in the pores is forcibly discharged into the surrounding liquid thus providing turbulent mixing of the bulk phase liquid when the belt-to-liquid volume in the tank is high. This turbulence is also useful in maintaining particulate matter in suspension when the feed is a slurry or contains organic debris. Prior art requires an independent source of agitation. Packed beds of sorption resin tend to become occluded by extraneous particulates in the feed. In fluidized bed systems, the adjustment of throughput to balance resin hold-up with contaminant particle passage is difficult to control; it results in process inefficiencies. The present invention, by using large-pored resins and continuous vigorous flushing action, permits sorption separation in the presence of certain non-abrasive, high-solid slurries or pulps. With the appropriate choice of resin, the present invention may be used to remove slow-settling particles from suspension (e.g. tertiary-amine pendent groups for clay mineral removal).

As the compressed portion of the belt emerges from between the pressure rollers, it expands, creating a partial vacuum within it which is filled by the inrush of bulk phase liquid. This sudden movement of liquid contributes further to mixing in the external solution. Micro-eddies of the entering solution repeatedly contact the concave membrane walls of the quasi-spherical cells of the sorption resin, resulting in direct mass transfer of solute from the fluid phase to the solid phase. Thus, diffusion is substantially eliminated as a rate-limiting factor in mass transfer between phases. As required by a particular application, the belt may proceed through a plurality of sets of pressure rollers in each solution to optimize the resin-loading step in the separation process.

The composition of the feed solution (e.g. pH, ionic strength, and organic solvent content) is adjusted to maximize sorption of certain chemicals and to minimize the sorption of others. This allows the extraction of either the product or impurities from the feed solution. While prior art processes are generally limited in the concentration and viscosity of the feed solutions they are capable of handling, the continuous internal pumping action of the present invention allows the processing of highly concentrated and viscous solutions without resolution problems caused by precipitation and channeling or throughput limitations caused by pressure drops. Auxiliary pumps are unnecessary since pumping occurs as a natural consequence of the compression and release driven by belt movement.

After emerging from the feed solution, the belt moves through one or more sets of pressure rollers to express excess liquid or in some cases to facilitate the exchange of internal gasses with bulk phase gasses. The removal of all liquid but a laminar film on membrane surfaces reduces the mixing of feed and elution liquids thereby avoiding the problem of "axial mixing" of liquids which tend to be carried over from one solution to the next in interstices and micropores in prior art sorption separation processes. This feature of the invention also reduces the volume of solvents and reagents needed in the various steps.

After passing over a power roller, the belt is supported and directed by one or more idler rollers to the first elution step. The composition of the eluent is chosen to desorb one but not the other of the sorbed solutes by the adjustment of such factors as pH, ionic strength, organic solvents or specific substances that compete with the particular solute for sorption sites. The belt passively fills with eluent liquid as it enters the tank; then elution is facilitated by the turbulent flow of eluent from the belt as it is compressed between a pair of rollers. Elution is further facilitated by the turbulent flow entering the belt as it expands after passing through the rollers. This process is repeated as many times as necessary through a plurality of sets of rollers. After emerging from the eluent, the belt passes through a set of rollers to express excess eluent. Whereas most industrial chromatographic separations result in dilution, the present invention, generally, provides volume reduction simultaneously with separation.

One or more idlers guide the belt to the second elution step where the eluent composition has been designed to desorb the second product. Similar operations can be designed for the sorption and desorption of more than two products, and the products need not be limited to either the most strongly or most weakly sorbed substances as in the case in most continuous chromatographic methods. Unlike current column chromatographic methods, the present invention does not require significantly more time to process strongly adsorbed products than it does to process more weakly adsorbed products.

After the belt leaves the final elution tank, excess liquid is expressed by a set of nonsubmerged rollers. The belt may be run through a wash or regeneration solution before returning to the feed tank to complete the cycle. In many cases, however, a washing step can be eliminated because the small amount of liquid carried over is rapidly diluted in the next step.

Because of the significant reduction in the volume of liquid reagents required compared to current sorption methods, the present invention can reduce the waste streams of separation processes and contribute in this way to the environmental and economic goals of management.

Process Optimization

One of the greatest economic benefits of the present invention derives from the ease, simplicity and speed with which optimum conditions for sorption and desorption of target substances can be determined empirically. Engineering predictions in sorption-based separation processes are difficult because of inhomogeneity of resin particles, nonspecific multimodal sorption effects of resins, undetermined ionic complexation and other interactions among solutes, effects of solvation on diffusion, and the phenomenon of pore diffusion among others.

Experimental runs which require hours or days with standard column chromatography, and minutes to hours with high performance liquid chromatography, can be performed in seconds to minutes with the present invention. Since diffusion is not limiting, and mixing is thorough and essentially instantaneous, sorption conditions can be optimized by applying temporal gradients of various parameters in feed solutions while continuously monitoring the concentration of product in the effluent from the elution tank where the eluent has been adjusted for maximum desorption. Eluent conditions can be optimized similarly for a given apparatus conformation. Both time and money can be saved on research and development work using this method with the present invention. Bench-top models of the apparatus can also be used in basic chemical and biotechnology research, especially in the physical chemistry of proteins.

Scaleup

Reliable scaleup from bench-top, through pilot plant, to production model apparatus has, historically, been a severe problem in separation technology. Throughput in the present invention is controlled by three factors: 1. flow rate of feed and eluent streams; 2. belt speed; and 3. belt width and thickness. Because conditions within any cross section of belt are substantially uniform during any operational step, the data derived from small bench-top models are valid for the same conditions in production models which differ only in belt width and thickness. This does not obtain with prior art apparatus.

Embodiment for Demineralization of Water

Figure 2A:
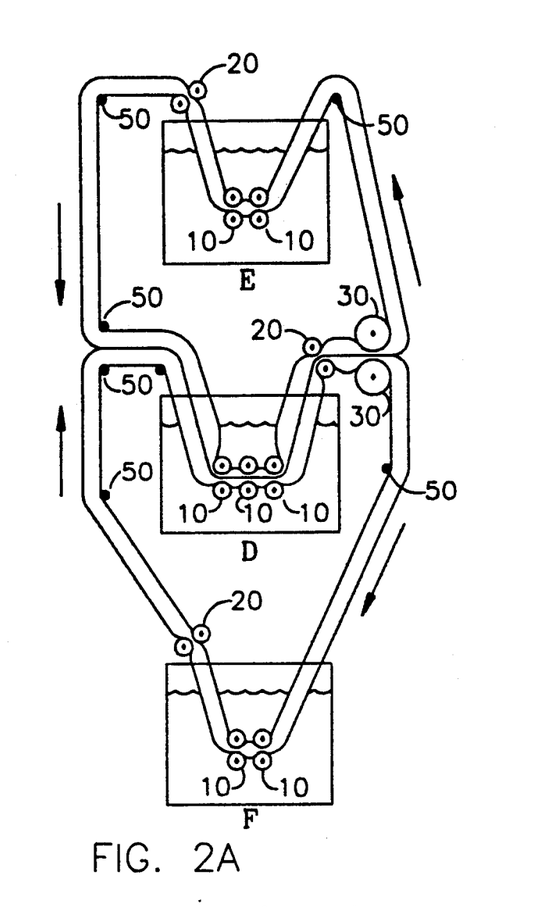
FIG. 2a illustrates a longitudinal section of a variant of the present invention which uses a bilayer belt in the demineralization of water.

By means of another preferred embodiment, the present invention also allows for a simple apparatus and method for continuous, mixed-bed, ion-exchange demineralization of water. FIG. 2a illustrates such an apparatus using a belt comprising two separable layers. The belt is composed of resilient open-cell polymer foam, one layer of which is a cation exchange resin and the other is an anion exchange resin.

The belt enters the feed tank with the two layers appressed and functioning as a single belt. Cations and anions are loaded onto their respective portions of the submerged belt by mass transfer from the feed solution as the belt is compressed and released while passing through one or more sets of pressure rollers. Cations from the water displace hydrogen ions from the cation exchange resin, and anions from the water displace hydroxyl ions from the anion exchange resin. The two products combine in the feed tank to produce water in a reaction that goes to completion, thus preventing back reactions that can occur when the two resins are contacted separately with the feed solution.

As the belt exits the feed solution, pressure rollers express the excess liquid. Following passage between two power rollers, the two portions of the moving belt separate before each enters the appropriate regeneration solution in separate tanks. Each submerged resin passes between one or more sets of pressure rollers before exiting the regeneration solutions. After exiting the regeneration solutions excess liquid is expressed from the belts; then the two portions of the belt are reunited before entering the feed tank to complete the cycle.

The advantages of the mix-bed ion-exchange application of the present invention include the production of ultra-pure water for the first time by a truly continuous process. An attendant reduction in capital outlay results from the smaller simpler apparatus which obviates complex valves and control equipment. In cases where feed solutions are variable, constant quality can be maintained by the cross-flow method described above. That method involves introducing the feed to one side of the belt and introducing the regenerant solution from the opposite side of the belt, allowing belt speed to be automatically adjusted to maintain a constant electrical conductivity in the product.

Embodiment for Liquid/Gas Phase Transfer

The applications described above involve mass transfer from a liquid phase to a solid phase. The present invention also incorporates applications involving mass transfer from the liquid to the gas phase—e.g. distillation, stripping and evaporation—and conversely, mass transfer from the gas phase to the liquid phase—e.g. product recovery, gas purification and deodorizing. In these applications, the resilient, open-cell polymer foam material of the belt is not directly involved in the mass transfer but serves as a support for the liquid film which is directly involved in the transfer. Hydrophilic polyurethane material can be used in these applications. The process of compression and release of the submerged belt is an integral part of the operation because it facilitates regeneration of the virgin film and removal of the pregnant film in product recovery and gas purification. The opposite process occurs in the stripping of volatile organic compounds from a liquid, i.e. the belt passes through a pregnant feed solution where it is loaded. Upon emerging from the solution, it passes through a set of rollers whereby excess liquid is removed.

Gas exchange between the liquid film on the polymer membrane surface and the bulk gas phase can be facilitated by passing the belt through a plurality of sets of compression rollers where turbulent gas flow out of and into the foam occurs. In some applications, for example the sorption of components of flue gas by a liquid film, a partial compression of the belt both laterally and horizontally as it enters and exits the gas phase exchange zone may be advantageous. The openings in the flue through which the belt passes should be slightly smaller than the belt in both cross-sectional dimensions. In most cases, compression of the moving belt forms a back-pressure seal outside the entrance to the flue and inside the flue at the exit, thus retarding the loss of flue gas. This is an unexpected and beneficial consequence of the invention.

Although the surface area per unit mass or volume of PUF is small relative to that of sorption resin particles, it is large relative to the surfaces currently used in industrial distillation and evaporation apparatus. Effective surface area is augmented in the present invention by the continuous regeneration of film surface and by the micro-turbulent flow of gas at the liquid/gas interface. Low-temperature fractional distillations can be carried out as a continuous process in a single apparatus, as the belt travels from chamber to chamber encountering carrier gas of progressively higher temperatures. This is made possible by the low heat capacity of the polymer support and liquid film. The rapid heat exchange between gas and liquid phases provided by the present invention results from the large membrane surface of the open-cell foam coupled with the turbulent gas flow through the moving belt. In the distillation-liquid feed tank, the belt passes through sets of rollers where turbulent flow insures that the liquid film on the resin is replaced by the feed solution. Excess feed solution is expressed from the belt after leaving the tank by a set of pressure rollers. After the belt traverses the distillation chambers, any residual liquid on the belts is washed away by passage through rollers submerged in a small volume of one of the more volatile components of the feed solution. The wash solution can be recycled through the system.

The present invention provides a smaller, more efficient apparatus for multiple liquid-to-gas and gas-to-liquid mass transfer operations than does the current technology. This capital saving derives from the higher surface to volume ratio of the film support material and from the fact that multiple separations occur within one unit, obviating the expense of additional materials-handling and control equipment. Additional advantages will be apparent to those skilled in the art.

Bioreactor Embodiment

The present invention provides an apparatus and method for the continuous cultivation of cells including bacteria and yeasts as well as shear-sensitive cells of filamentous fungi, plants, insects and mammals among others. Homogeneous bioreactors are oxygen-limited; they subject cells to shear stress. The productivity of existing heterogeneous bioreactors is limited by gradients in oxygen, nutrients, wastes, products, and heat. The application of a continuous, extractive, belt bioreactor of resilient open-cell foam polymer as described herein substantially eliminates these and other problems.

According to the present invention, conditions in any given cross-section of the moving belt are substantially homogeneous throughout the cycle. Oxygen, carbon dioxide and heat are freely exchanged through the thin film of nutrient solution covering the cells immobilized on the polymer membranes. In the simplest embodiment of the invention—for bacteria or yeasts—transfer of dissolved nutrients to the immobilized cell layer results from partial compression of the soft belt as it passes between submerged pressure rollers. After exiting the nutrient solution, the belt is partially compressed again by another set of pressure rollers to remove excess liquid and by a plurality of similar sets or rollers to facilitate heat and gas exchange. Gas exchange can also be accomplished by blowing a stream of gas to flow through the belt. In the case of alcoholic fermentation by yeasts, removal of volatile ethanol from the culture medium by this process allows for higher productivity and obviates the necessity of using only alcohol-tolerant strains. In the wash tank, product, wastes, free cells and debris are removed from the belt as it passes through one or more sets of submerged pressure rollers adjusted to the appropriate nip.

Figure 3A:
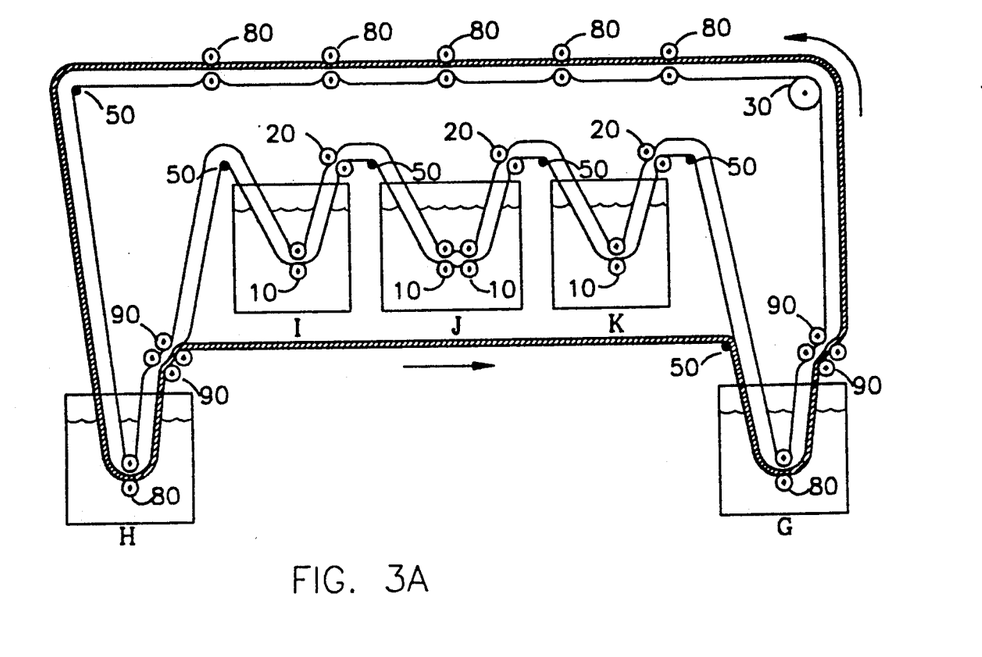
FIG. 3a is a transverse sectional view of a bioreactor which employs a two-layer belt within the scope of the present invention.

The particular bioreactor embodiment of the invention illustrated in FIG. 3a simultaneously cultures shear-sensitive cells, removes wastes, and extracts secreted products such as antibody, hormone, or enzyme proteins. The culture, waste removal, and product extraction functions are continuous. An important feature of this embodiment is the use of a separable bilayer belt, one layer of which is semi-rigid and the other soft and preferably more than twice as thick as the first. The semi-rigid portion of the belt carries the immobilized cells and follows a circuit more or less similar to that described above for belt in the embodiment for shear-insensitive cells but with little or no compression during passage through the pressure rollers. The soft portion of the belt, however, is compressed by the rollers and impels the movement of both liquid and gas through the semi-rigid portion of the belt. The soft portion can also contain bioaffinity ligands (e.g. dyes, antibodies, substrates, receptors, chelates or toxins and the like) for the specific adsorption of the product. Less specific sorption resins, for example ion-exchange or hydrophobic resins, may also be used.

As the belt traverses the distance between the nutrient tank and the wash tank, carbon dioxide and ammonia generated by cell metabolism are transferred to the bulk gas phase. Oxygen passes from the bulk gas phase to the liquid film covering the cells, facilitated by the pumping action of the pressure rollers on the soft portion of the belt. At the same time, the cells are consuming nutrients and secreting product molecules and soluble wastes into the liquid film. Upon reaching the wash tank, soluble wastes and debris are removed from the belt by the flushing action of the rollers, and product molecules are transferred to the product-specific bioaffinity ligands in the soft portion of the belt.

After emerging from the wash solution, excess liquid is expressed from the belt by pressure rollers, and the two protions of the belt separate. The semi-rigid, cell-bearing portion proceeds directly to the nutrient tank, and the soft bioaffinity resin portion enters the first elution tank.

The composition of the first eluent is such that molecules sorbed nonspecifically to the belt are desorbed and removed by passage of the belt between pressure rollers. After excess eluent is removed by nonsubmerged pressure rollers, the soft portion of the belt enters the main elution tank. Here an excess of unbound bioaffinity ligand, or some other chemical swing, desorbs the product from the resin, and the product is removed from the belt by compression during passage through pressure rollers. Following a final wash to remove eluent, the bioaffinity portion of the belt rejoins the cell-bearing portion before entering the nutrient tank to complete the cycle.

The advantages of the above embodiment are many and diverse. Oxygen supply is not a limiting factor in this bioreactor because diffusion is reduced to a minimum and oxygen is delivered by turbulent flow of a high capacity gas carrier, not by low capacity aqueous solution. Expensive nutrients are supplied only in the amount and at the time needed, thereby optimizing efficient utilization and reducing waste streams. Production is not inhibited by excess nutrients. Cells are provided with a more or less natural environment where metabolite gradients can be established within multiple layers of cells. Potentially toxic wastes are removed quickly and continuously. Product is removed quickly and continuously, thereby avoiding product inhibition of production and product degradation. The quick removal of product also avoids slow denaturing of proteins by nonspecific adsorption reactions. Sterilization of the entire system is less costly than prior art systems, which require a larger volume of aqueous solutions and massive equipment capable of sustaining relatively high hydrostatic pressure. The bioreactors of the present invention require less capital outlay for many reasons including the facts that they are smaller, they are constructed of less expensive materials, and they require less complex equipment and control systems.

Additional Objects and Advantages

It is clear that the present invention overcomes the mass transfer limitations of prior art continuous belt apparatus. Some additional objects and advantages over prior art are listed below while still others will occur to those skilled in the art.

General

An object of the present invention is a system of standardized modules which can be easily adapted to perform a variety of chemical separations, chemical reactions, and bioreactor functions with the advantage of low capital outlay and fast startup for new processes.

An object of the present invention is an apparatus that is easily constructed from mechanically simple elements which are readily available with the advantage of quick startup, low capital investment and low operating costs.

An object of the present invention is a reactor in which gas exchange occurs in a liquid film, not in a bulk liquid phase, with the advantage of reduced energy requirements and reduced foaming.

An object of the present invention is a reactor which is substantially self-cleaning by operation with cleaning solutions and live steam or both with the advantage of low labor costs and fast turnaround time.

An object of the present invention is a reactor in which throughput is not limited by pressure drop with the advantage of high flow rates using equipment of light construction.

An object of the present invention is a reactor in which heat generated in solutions by exothermic reactions is dissipated by evaporative cooling at liquid film surfaces and by ready heat exchange with the bulk gas phase.

An object of the present invention is an apparatus for the continuous drying of nonpolar solvents by cation exchange belts and continuous thermal regeneration with the advantage of efficient integration with other continuous processes.

An object of the present invention is a reactor in which the resin is continuously and vigorously washed during production with the advantage that precipitates such as silicates, metal hydroxides, calcium sulfate, organic slimes, and other particulate matter are physically removed from the resin thereby avoiding fouling.

Sorption

An objective of the present invention is a sorption separation process in which the universal interdependency among resolution, flow, and capacity in prior art methods is broken by adding a fourth factor, belt speed, with the advantage of optimizing each element independently.

An object of the current invention is a reactor in which all resin surfaces are available to large molecules, unlike reactors with porous particulate resins, with the advantage of maximum use of resin inventory.

An object of the present invention is a reactor in which the kinetic energy of turbulent flow provides rotational energy to large solute molecules with the advantage that solute binding to regiospecific ligands is facilitated.

An object of the present invention is a reactor in which sorption ligands with low binding energies can be used effectively because of rapid continuous resin regeneration with the advantage that mild desporption conditions reduce denaturation of biosolutes.

An object of the present invention is a reactor which, unlike fluidized bed sorption processes, can completely remove solutes from particulate-containing feeds with the advantage of combining high throughput with single-stage separation from such solutions.

An object of the present invention is a sorption reactor that can operate efficiently at cold temperatures because diffusion is not limiting with the advantage of energy savings.

An object of the present invention is a sorption reactor which is not disturbed by degassing of solutions with the advantage of decreased operational cost by deletion of solution degassing steps.

An object of the present invention is a continuous-sorption reactor in which resin transfer between process steps is simple, requiring no pumps or complex valves, with the advantage of lower capital outlay and lower maintenance costs.

An object of the present invention is a sorption reactor in which the critical desorption concentration of the eluent is established instantaneously and maintained continuously throughout the cross-section of the resin belt during elution steps.

An object of the present invention is a sorption separation process which is brief, thereby avoiding slow reactions such as aggregation and self-assembly between the monomeric forms of product proteins, with the advantage of more dependable product resolution and recovery.

An object of the present invention is a method for sorption separation in which protein molecules are exposed to the sorbent for a short period, thus reducing the competition between one-site and multiple-site binding, with the advantage of increasing the effective capacity of the resin.

An object of the present invention is a sorption separation method in which a large excess of eluent to enhance diffusion is not necessary with the advantage of reduced reagent cost.

An object of the present invention is a sorption separation process in which diffusion parameters need not be considered in selecting an eluent with the advantage of greater process efficiency.

An object of the present invention is a sorption separation method in which the short time lapse between uptake and wash or regeneration avoids slow nonspecific chemisorption reactions with the advantage that fouling of the resin is avoided.

An object of the present invention is a sorption separation reactor in which sorption capacity can be increased at the beginning of a run by using a thicker belt or during a run by increasing belt speed with the advantage of accommodating greater variation in feed composition than does prior art.

Ion-Exchange

An object of the present invention is a continuous method for the sorption of large hydrated ions (e.g. uranium dioxide, silver, cesium and rubidium) since internal pore space of the resin is not limiting with the advantage that these ions can be selectively sorbed on the basis of chemical characteristics.

An object of the present invention is an ion-exchange method which can be operated efficiently at low temperature with the advantage that the life of quaternary ammonium ion exchange resins is prolonged.

Bioreactor

An object of the present invention is a bioreactor with simple, robust, interchangeable parts providing the advantage of reduced delays due to mechanical failure.

An object of the present invention is a bioreactor constructed of light materials of low heat capacity with the advantage of short heating and cooling periods and low energy consumption during steam sterilization.

An object of the present invention is a bioreactor in which nutrient liquids are confined to internal tanks and belts and therefore do not contact external barriers thereby providing the advantage of minimizing microbial contamination.

An object of the present invention is an immobilized-cell bioreactor that can be steam sterilized in situ, then seeded directly with cell suspensions, so that intermediate inoculum transfer steps can be deleted with the advantage of reduced microbial contamination and faster turnaround time.

An object of the present invention is a bioreactor in which antibiotics can be dissolved in the reactive surfaces for slow release with the advantage of efficient use of these expensive compounds to prolong the operational life of a culture.

REFERENCE NUMERALS 10 set of full-submerged, full-compression pressure rollers
20 set of nonsubmerged, full-compression pressure rollers
30 power roller
40 single-layer belt
50 idler roller
60 two-layer ion-exchange belt
64 cation exchange layer of belt
68 anion exchange layer of belt
70 two-layer extractive bioreactor belt
74 semi-rigid cell-immobilization layer of belt
78 soft bioaffinity layer of belt
80 set of submerged, partial-compression pressure rollers
90 set of nonsubmerged, partial-compression pressure rollers
Tanks
A feed solution
B eluent solution
C regeneration solution
D feed solution
E cation exchanger regeneration solution F anion exchanger regeneration solution
G nutrient solution
H waste removal solution
I contaminant eluent solution
J product eluent solution
K regeneration solution

DETAILED DESCRIPTION OF PREFERRED EMBODIMENTS

Sorption Separator Embodiment

A preferred embodiment of the present invention is the sorption separation apparatus illustrated in FIG. 1a. The essential physical elements of the invention are one or more sets of pressure rollers (10) submerged in at least one liquid, one or more sets of pressure rollers (20) not submerged in a liquid, a power roller (30), and a continuous belt (40) of resilient open-cell foam polymer which is caused to move through sets of rollers where it is alternately compressed and released. It should be noted that the scope of the invention also includes static means of belt compression and any means causing cyclic movement of the belt. Idler rollers (50) may be included to control the belt movement; various tanks, ducts and fluid control mechanisms may be present in some applications but are not considered to be essential elements of the core invention disclosed herein.

In order to facilitate understanding of the physical structure of the apparatus and the method of operation of the present invention, a detailed example from hydrometallurgy is described in which gold, silver, and iron are sequentially separated from solution. The chemical conditions referred to in the example are taken primarily from the recent work of Caletka et al (Caletka, Hausbeck and Krivan, 1990). The resilient open-cell foam polymer is, in this case, polyether-type polyurethane foam. The feed in tank A consists of an aqueous solution of 0.2M HCl in which 25 ppm each of pure gold(III), silver(I) and iron(III) are dissolved. The eluent in tank B is 1M HCl. The eluent in tank C is acetone.

Figure 1B:
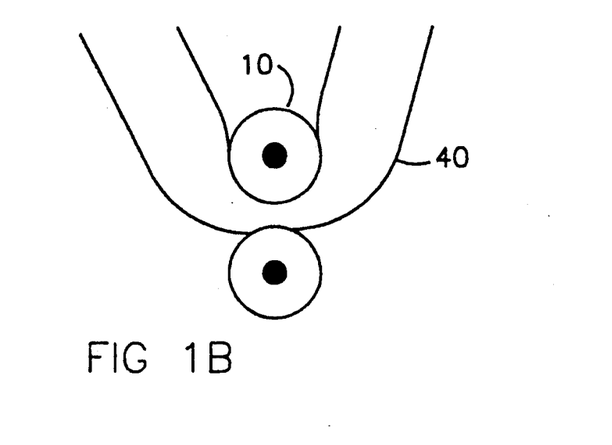
FIG. 1b shows an enlarged longitudinal section of a portion of belt with submerged pressure rollers.

The operation of the present example is effected by causing power roller (30) to move the belt (40) in the counterclockwise direction, so that during each cycle every part of the belt becomes immersed in the feed solution in tank A, and solution passively fills the pores of the belt. The belt is compressed as it moves between the submerged pressure rollers (10) as shown in detail in FIG. 1b. The resulting turbulent flow of feed solution out of the belt causes intimate contact of solution and resin membrane, thereby enhancing mass transfer of the solute to the membrane. Further solute transfer from bulk phase solution to the resin occurs upon release from compression when solution rushes into the belt. This rapid solute loading of the belt occurs with each passage through a set of submerged rollers. Under the conditions of the present example, the gold and silver chloride complexes are strongly sorbed by the polyurethane belt while the iron remains in the feed solution.

Upon emergence from the feed solution, the belt passes between pressure rollers (20) which are not submerged in liquid, whereby excess feed solution is expressed and returned to tank A. After passing over the power roller (30) where translational energy is imparted to the belt, the belt passes over an idler roller (50), enters tank B, and is passively filled with the first eluent liquid, aqueous 1M HCl.

The solute-loaded belt then passes through one or more sets of submerged pressure rollers (10), in this case three sets, where silver is eluted from the belt while gold is largely retained. The physical details of the hydrodynamic processes within the belt during elution are substantially as described for resin loading in the feed solution. After the belt exits the first eluent, excess liquid is squeezed from the belt by a set of pressure rollers (20). The belt then moves over an idler (50) and descends into the final eluent, acetone, in tank C. Here gold is removed from the belt, and regeneration of the resin is completed. Excess acetone is removed by passage through rollers (20) above tank C, and the belt is directed over an idler (50) and into the feed solution in tank A to complete the cycle.

Demineralizer Embodiment

Figure 2B:
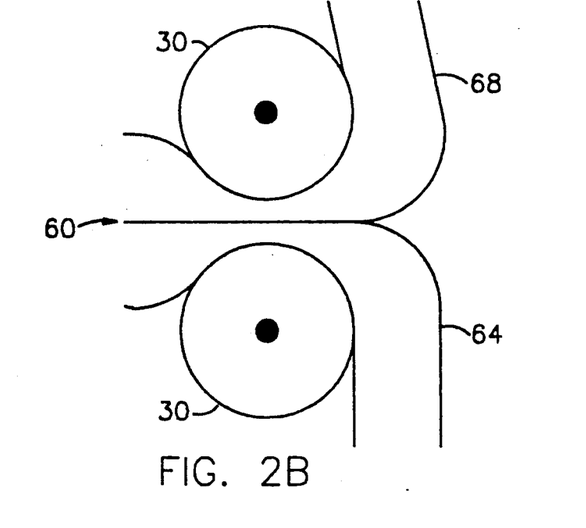
FIG. 2b represents an enlarged longitudinal section of a portion of a separable two-layer belt with power rollers.

FIGS. 2a and 2b demonstrate an embodiment of the present invention for the demineralization of water. The important physical elements of this example are similar to those described in FIG. 1a, namely, sets of submerged pressure rollers (10), sets of pressure rollers (20) not submerged in a liquid, a pair of power rollers (30), and a continuous belt of resilient open-cell foam polymer. In this case, however, the belt (60) comprises two separable layers, one a cation exchange resin (64) and the other an anion exchange resin (68), illustrated in FIG. 2b. And again idlers (50) are incidentally included as belt guides.

The operation of the demineralization embodiment taught by the present invention is similar to the operation of the apparatus in FIG. 1a. The feed tank D in this example contains an aqueous solution of minerals. The bulk phase liquid flows turbulently within the resin as the belt (60) passes through three sets of pressure rollers (10). Cations in the bulk solution displace hydrogen ions on the cation-exchange layer of the belt (64), while anions in the bulk solution displace hydroxyl ions on the anion-exchange layer of the belt (68). The displaced hydrogen and hydroxyl ions combine in the well-mixed solution to form water as the only product. Excess liquid is expressed from the belt (60) by pressure rollers (20) located above the tank.

After the belt (60) passes between the power rollers (30), the two portions of the belt separate. Subsequent to passing over idlers (50), the cation-exchange layer (64) enters tank E which contains hydrochloric acid, and the anion-xchange layer (68) enters tank F which contains sodium hydroxide. Sets of submerged pressure rollers (10) facilitate regeneration of the resins by causing turbulent flow of bulk solutions within the belts, so that the cation and anion exchange sites are recharged by displacing the adsorbed cation and anion minerals with hydrogen and hydroxyl ions respectively. Both layers of the belt are squeezed free of excess regenerant as they pass through pressure rollers (20) above each tank. The cation layer (64) and the anion layer (68) reunite as they pass over an idler (50) before reentering the feed tank D to complete the cycle.

Continuous Extractive Bioreactor

Figure 3B:
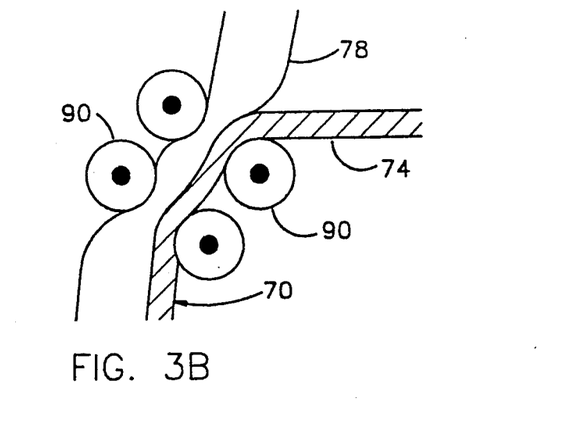
FIG. 3b shows an enlarged longitudinal section of a portion of a separable two-layer belt comprising soft and semi-rigid layers with two sets of nonsubmerged pressure rollers.

FIGS. 3a and 3b illustrate a continuous extractive bioreactor according to the present invention. The important physical elements of this embodiment are submerged pressure rollers (10) and nonsubmerged pressure rollers (20), both adjusted for full compression; submerged pressure rollers (80) and nonsubmerged pressure rollers (90), both adjusted for partial compression; a pair of power rollers (30); and idler rollers (50). The most important element is the resilient open-cell foam polymer belt (70) which comprises two separable layers: a semi-rigid layer (74) on which cells are immobilized, and a soft layer (78) approximately twice as thick as the other and bearing pendent groups with a special affinity for the product (FIG. 3b).

In this particular example, mammalian cells are used to produce an enzyme which is specifically adsorbed because of its affinity for a synthetic dye attached to the soft polyether-polyurethane portion of the belt (78). Tank G contains the nutrient solution, tank H the wash solution. Tank I contains the eluent for desorbing the nonspecifically sorbed substances. Tank J contains an excess concentration of free dye molecules for displacement of the enzyme from the dye molecules bound to the resin. Tank K contains a wash solution for the removal of the excess free dye and other extraneous compounds.

The operation of the continuous extraction bioreactor of the present example is similar that of the demineralizer embodiment shown in FIG. 2a. The bilayer belt (70), moving in a counterclockwise direction, enters the nutrient solution in tank G, whereupon its pores passively fill with liquid. As the bilayer belt passes through a set of pressure rollers (80), only the soft layer of the belt (78) is compressed, but the outflow from the soft layer impels nutrient solution through the semi-rigid layer of the belt (74). Upon exiting the rollers, the inrush of liquid into the re-expanding soft layer of the belt draws nutrient solution into the semi-rigid layer of the belt. At the membrane surface, any residual solution from previous steps is displaced by nutrient solution. After emerging from the nutrient solution, the belt moves through two sets of pressure rollers (90) with the nip adjusted so that only the soft layer of the belt (78) is compressed, while the semi-rigid layer of the belt (74) is not substantially compressed. Passage through the first set of such rollers causes the liquid to be evacuated from the soft portion. The gas pressure generated by compression of the soft layer in the second set of rollers expels excess liquid from the semi-rigid layer of the belt.

During passage of the belt over the power roller (30), translational energy is imparted to the belt. Exchange between the oxygen-rich bulk-phase gas and pore-space gas enriched in carbon dioxide and ammonia occurs as the belt moves through a plurality of pressure rollers (80) adjusted so that only the soft layer of the belt is compressed. The pressure generated by compression of the soft layer causes turbulent flow of gases through the semi-rigid layer of the belt. The process cycle can be prolonged by reducing belt speed or by extending the belt length and adding additional sets of pressure rollers (80).

Passage over an idler roller (50) directs the belt into tank H which contains the wash solution for removal of soluble wastes. As the belt passes through submerged pressure rollers (80), the liquid surrounding the cells, immobilized in the semi-rigid layer of the belt (74), is exchanged by turbulent flow with the bulk wash solution; product molecules are transferred to specific binding sites in the soft layer of the belt (78).

The belt (70) emerges from the wash solution and passes through two sets of rollers (80) whereby excess liquid is removed from both layers. The two layers of the belt separate, with the soft layer (78) directed to tank I and the semi-rigid layer (74) directed to feed tank G by idler rollers (50).

In tank I, substances which are bound nonspecifically to the resin are removed by turbulent flow of the eluent through the belt (78) as it is fully compressed by pressure rollers (20) and released. After exiting tank I, excess liquid is again removed by compression between pressure rollers (20). Passing over an idler (50), the belt is immersed in the free dye solution of tank J. The product molecule is displaced from the resin-bound dye by the free dye as the bulk phase solution is repeatedly pumped through the belt by movement through two sets of pressure rollers (20). As before, excess liquid is expressed from the belt before it enters the next tank, K. The wash liquid in tank K substantially removes residual dye solution and other substances to regenerate the resin for the next cycle. Following removal of the regenerant solution by pressure rollers, an idler roller directs the belt toward the feed tank G.

The regenerated soft layer of the belt (78) and the semi-rigid layer of the belt (74) bearing the cells reunite and pass over an idler roller and into the nutrient solution in tank G to complete the cycle.

The particular examples described in detail above represent only a few of the many possible beneficial uses of the present invention the full scope of which is defined by the following claims.

I claim:

1. An apparatus for facilitating mass transfer between fluid and solid phases, the apparatus comprising:
    (a) a continuous first belt of resilient, open-cell foam polymer;
    (b) first drive means associated with the first belt for continuously guiding and driving the first belt such that each point along the length of the first belt passes through a first fluid, then through a second fluid contained in a separate second container, and then back to the first fluid;
    (c) first compression means for compressing and then releasing the first belt at a point at which the belt is submerged in the first fluid; and
    (d) second compression means for compressing and then releasing the first belt at a point at which the first belt is submerged in the second fluid.

2. The apparatus of claim 1 further comprising:
    (a) first exit compression means for compressing and then releasing the entire width of the first belt at a point immediately after the first belt exits the first fluid; and
    (b) second exit compression means for compressing and releasing the entire width of the first belt at a point immediately after the first belt exits the second fluid.

3. The apparatus of claim 1 wherein:
    (a) the first compression means is capable of compressing and releasing the first belt successively at a plurality of points at which the first belt is submerged in the first fluid.

4. The apparatus of claim 3 wherein:
    (a) the second compression means is capable of compressing and releasing the first belt successively at a plurality of points at which the first belt is submerged in the second fluid.

5. The apparatus of claim 1 wherein:
    (a) the first and second compression means compress and release the first belt along an entire width thereof.

6. The apparatus of claim 1 wherein:
    (a) the first belt includes a sorbent material attached thereto within the open cells of the material from which the first belt is formed.

7. The apparatus of claim 1 wherein:
    (a) the first belt includes a catalyst material attached thereto within the open cells of the material from which the first belt is formed.

8. The apparatus of claim 1 further comprising:
(a) a continuous second belt of resilient, open-cell foam polymer;
(b) second drive means associated with the second belt for continuously guiding and driving the second belt such that each point along the length of the second belt passes through the first fluid and first compression means in a layered fashion adjacent to the first belt, through a third fluid contained in a separate third container, and then back to the first fluid, the first compression means compressing and then releasing the second belt simultaneously with the first belt at a point at which both the second belt and first belt are submerged within the first fluid; and
(c) third compression means for compressing and then releasing the second belt at a point at which the second belt is submerged in the third fluid.

9. The apparatus of claim 1 wherein:
(a) the first belt is comprised of a material capable of retaining shear sensitive material within the open cells thereof.

10. The apparatus of claim 1 wherein:
(a) the first compression means and the second compression means each comprise pressure rollers extending generally parallel to each other in position to compress the first belt as it passes therebetween.

11. The apparatus of claim 1 wherein:
(a) the first compression means and the second compression means each comprise static compression members.

12. A method for facilitating mass transfer between fluid and solid phases, the method comprising the steps of:
(a) driving a continuous first belt of resilient open-cell foam polymer material such that a point along the length of the first belt passes first through a first fluid, and then through a second fluid contained in a separate second container, before returning to the first fluid;
(b) compressing and then releasing the first belt at a point at which the first belt is submerged in the first fluid; and
(c) compressing and then releasing the first belt at a point at which the first belt is submerged in the second fluid.

13. The method of claim 12 further comprising the steps of:
(a) compressing and releasing the first belt successively at a plurality of points at which the first belt is submerged in the first fluid; and
(b) compressing and releasing the first belt successively at a plurality of points at which the first belt is submerged within the second fluid.

14. The method of claim 12 further comprising the steps of:
(a) compressing and then releasing the entire width of the first belt immediately after the first belt exits the first fluid;
(b) compressing and then releasing the first belt along its entire width immediately after the first belt exits the second fluid.

15. The method of claim 12 further comprising the steps of:
(a) driving a continuous second belt of resilient open-cell foam polymer material such that a point along the length of the second belt passes first through the first fluid and then through a third fluid in a separate third container before returning to the first fluid;
(b) compressing and releasing the second belt at a point at which the second belt is submerged in the first fluid; and
(c) compressing and releasing the second belt at a point at which the second belt is submerged in the third fluid.

16. The method of claim 15 wherein:
(a) the steps of compressing and releasing the first and second belts while submerged in the first fluid are performed by a set of compression rollers between which the first and second belts pass together in a layered fashion.

* * * * *